Figure 1:
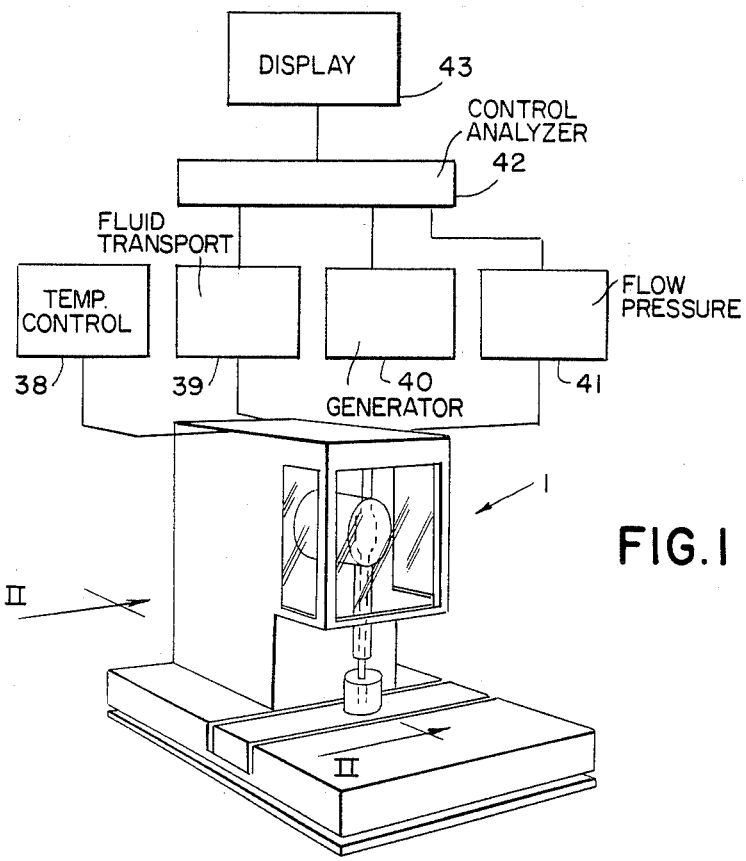

United States Patent [19]

Thurston

[11] Patent Number: 4,566,314

[45] Date of Patent: Jan. 28, 1986

[54] DEVICE AND METHOD OF MEASURING THE VISCOSITY AND/OR VISCO-ELASTICITY OF A FLUID

[76] Inventor: George B. Thurston, 1000 Madrone Rd., Austin, Tex. 78746

[21] Appl. No.: 675,522

[22] Filed: Nov. 28, 1984

[30] Foreign Application Priority Data

Dec. 2, 1983 [NL] Netherlands .................. 8304154

[51] Int. Cl.⁴ ............................................. G01N 11/08
[52] U.S. Cl. ........................................................ 73/55
[58] Field of Search ............................................ 73/55

[56] References Cited

U.S. PATENT DOCUMENTS 2,011,862 8/1935 Konheim et al. ..................... 73/55

FOREIGN PATENT DOCUMENTS 2482302 11/1981 France .
210470 4/1968 U.S.S.R. .................................. 73/55

OTHER PUBLICATIONS

G. B. Thurston, "Viscoelasticity of Human Blood", Biophysical Journal, vol. 12, (1972), pp. 1205–1217.
R. Zitny et al., "Continuous Recording of Flow Curves on a Capillary Rheometer Using a New Pressure Transmission Element", Jrnl. of Physics, E; Scientific Instruments, vol. 8, No. 3, (1975).

Primary Examiner—Stuart J. Levy
Assistant Examiner—Joseph W. Roskos
Attorney, Agent, or Firm—Arnold, White & Durkee

[57] ABSTRACT

A method and device for handling a fluid to accurately measure the viscosity and/or visco-elasticity of the fluid. More particularly, the method and device hereof is adapted for reliable calibration and filling with a subject fluid, such as blood, enabling accurate measurement even when only a small amount of the subject fluid is available for analysis. Broadly speaking, the device includes a measuring chamber filled with a standard fluid, a coupling chamber filled with a coupling fluid, a flexible diaphragm separating the chambers, and a measuring tube suspended in a downward direction from the coupling chamber. The measuring chamber includes a pressure and flow generating plunger and a pressure sensor; a flow sensor is operably coupled to the measuring chamber. Preferably, the measuring tube is filled with subject fluid by first drawing an air bubble into the tube and then drawing the subject fluid into the tube to completely fill the tube. The air bubble serves to separate the subject fluid from the coupling fluid. After the tube is filled, a fluid interface between the coupling fluid and subject fluid is formed with the air bubble rising upwardly through the coupling fluid to the top of the coupling chamber.

26 Claims, 6 Drawing Figures

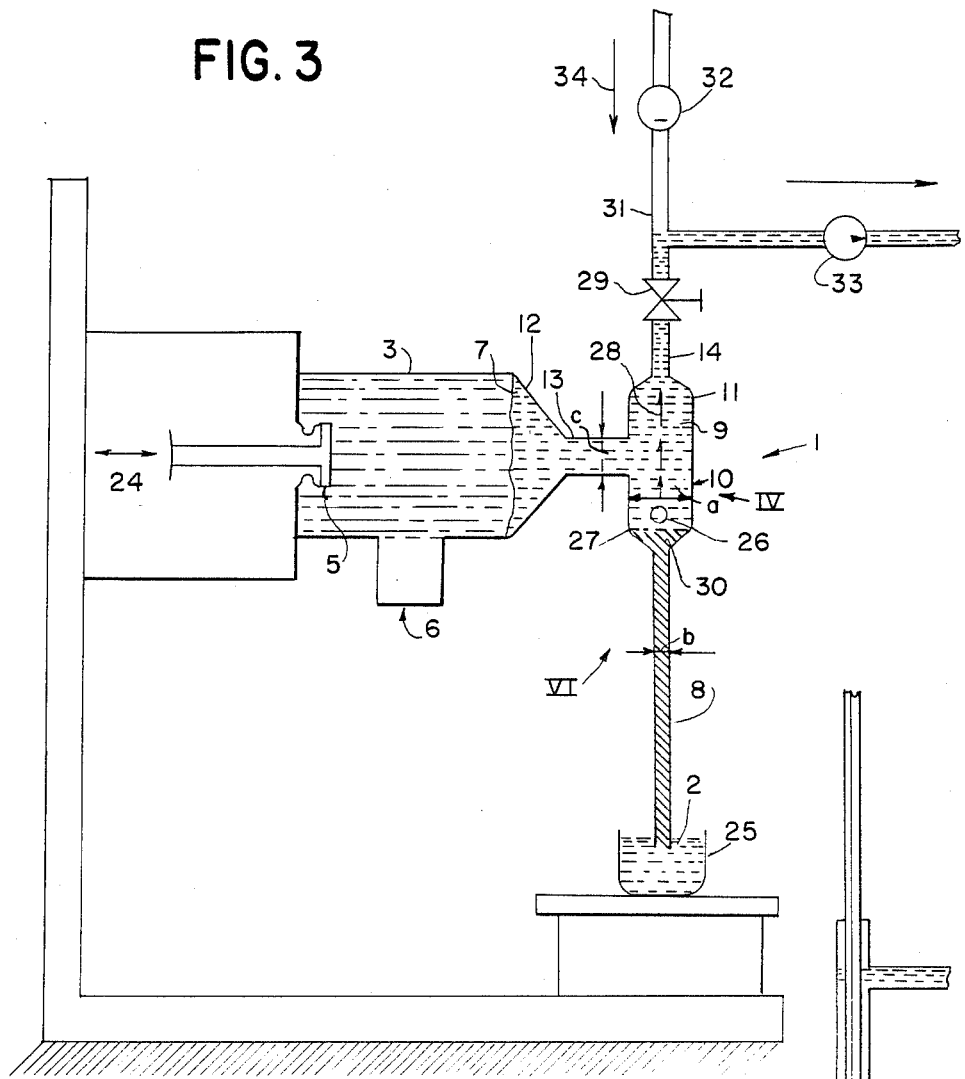
FIG. 3
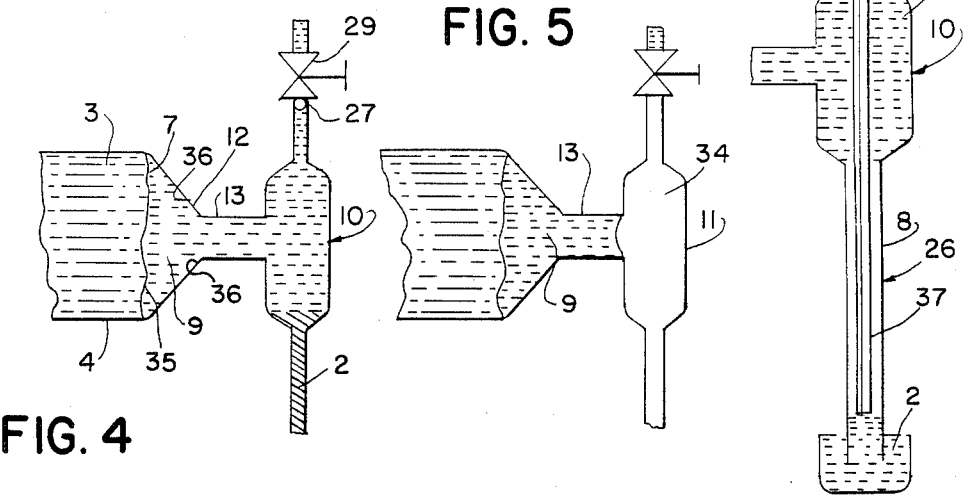
FIG. 4
FIG. 5
FIG. 6

DEVICE AND METHOD OF MEASURING THE VISCOSITY AND/OR VISCO-ELASTICITY OF A FLUID

The invention relates to an apparatus for measuring the viscosity and/or visco-elasticity of a fluid comprising: a measuring chamber that can be filled with a standard fluid and is provided with pressure generating means and with pressure sensing means and at least one measuring tube connected through a flexible diaphragm with the measuring chamber for receiving the fluid to be measured.

Such an apparatus is known and is described inter alia in Biophysical Journal (1972), Vol. 12, pages 1205 to 1217. In this known apparatus a plurality of measuring tubes are arranged above the measuring chamber and the fluid to be measured, in this case blood, extends from the diaphragm through the measuring tubes as far as above said measuring tubes. Therefore, this known apparatus has on the one hand the disadvantage that gas bubbles can be removed only with great difficulty in particular from the space between the diaphragm and the measuring tubes. On the other hand this known apparatus does not permit of measuring several types of fluids because these fluids are not tolerant of the material of the diaphragm, for example, due to corrosion phenomena and salt deposition in the case of physiologic solution. Since much time gets lost in removing gas bubbles, it is not or only hardly possible to measure the viscosity and/or visco-elasticity of unstable fluids accurately by means of the known apparatus.

The invention has for its object to improve an apparatus of the kind set forth in a sense such that the aforesaid disadvantages are eliminated as far as possible. According to the invention this is achieved in that with the interposition of a coupling chamber filled with a coupling fluid the measuring tube is connected with the diaphragm.

When the measuring tube is located mainly at a lower level than the measuring chamber, it is possible to include an air bubble between the fluid to be measured and the coupling fluid when the fluid to be measured is received in the measuring tube so that mixing of the two fluids is avoided as far as possible. Whereas, when the coupling chamber is being entered, the air bubble is removed from the interface preferably by choosing an inner dimension of the first coupling compartment to exceed the inner dimension of the measuring tube.

When the coupling chamber comprises a first coupling compartment connected with the measuring tubes, the air bubble is prevented for reaching the diaphragm.

When the coupling chamber comprises a second coupling compartment adjacent the diaphragm and being laterally connected with the first coupling compartment it is avoided that at a rise of the air bubble in the first compartment as a result of generated whirls the fluid to be measured should get into the second coupling compartment and would foul this coupling compartment. Moreover, when a connecting tube preferably connects the first with the second coupling compartment it is ensured that, when the first coupling compartment is being emptied, for example, for cleaning purposes, the second coupling compartment remains filled with coupling fluid so that this coupling compartment remains free of gas bubbles. In order to obtain the capillary effect of the coupling fluid required for this purpose in the connecting tube an inner dimension of the first coupling compartment preferably exceeds the inner dimension of the connecting tube.

A device that can be particularly easily controlled and cleaned is obtained when a conduit including a closing member and communicating with an air and/or fluid pump opens out in the coupling chamber.

The use of an air bubble separating the coupling fluid from the fluid to be measured may be dispensed with, when piston means adapted to reciprocate through the coupling chamber and the measuring tube are used for introducing the fluid to be measured into the measuring tube.

The second coupling compartment can be cleaned in a simple manner when a wall located opposite a side of the diaphragm remote from the second coupling compartment is converging in a direction away from the diaphragm. Therefore, by displacing the diaphragm towards said wall by increasing the pressure in the measuring chamber all coupling fluid and any impurities can be removed from the second coupling compartment and the second coupling compartment can be cleaned by introducing several times fresh coupling fluid and by the reciprocatory movements of the material produced with the aid of the pressure generating means.

The invention furthermore relates to an apparatus for measuring the viscosity and/or the visco-elasticity of a fluid comprising: a measuring chamber filled with a standard fluid provided with pressure generating means and with pressure sensing means, and at least one measuring tube connected through a flexible diaphragm with the measuring chamber for receiving the fluid to be measured and being characterized only in that a wall located opposite a side of the diaphragm remote from the measuring chamber is converging in a direction away from the diaphragm. With such an apparatus the above-described advantages regarding cleaning the second compartment can also be obtained.

The invention finally also relates to the measurement of the viscosity and/or the visco-elasticity of a fluid with the aid of the apparatus described above. The method embodying the invention is characterized in that from a holder the fluid to be measured, provided by separating material is introduced through the measuring tube into the coupling chamber and the separating material between the fluid to be measured and a coupling fluid is removed. Thus a mixing of coupling fluid and the fluid to be measured is avoided substantially completely. It is furthermore possible in this manner to use fluids of different specific weights, for example, in the case in which the coupling fluid has a higher specific weight than the fluid to be measured.

It is not necessary to remove the air bubble from the coupling compartment and it may be tolerated in the coupling chamber when the air bubble constantly occupies the same position and has the same dimensions so that its presence can be compensated for with the aid of calibration experiments. Therefore, the method embodying the invention is furthermore characterized in that the measuring tube is filled with a coupling fluid and the separating material is formed by an air bubble introduced into the measuring tube prior to the fluid to be measured, whilst as the case may be, the air bubble is admitted to the coupling chamber.

The above-mentioned and further features will be elucidated with reference to a few non-limitative embodiments of the invention shown in a drawings.

Figure 2:
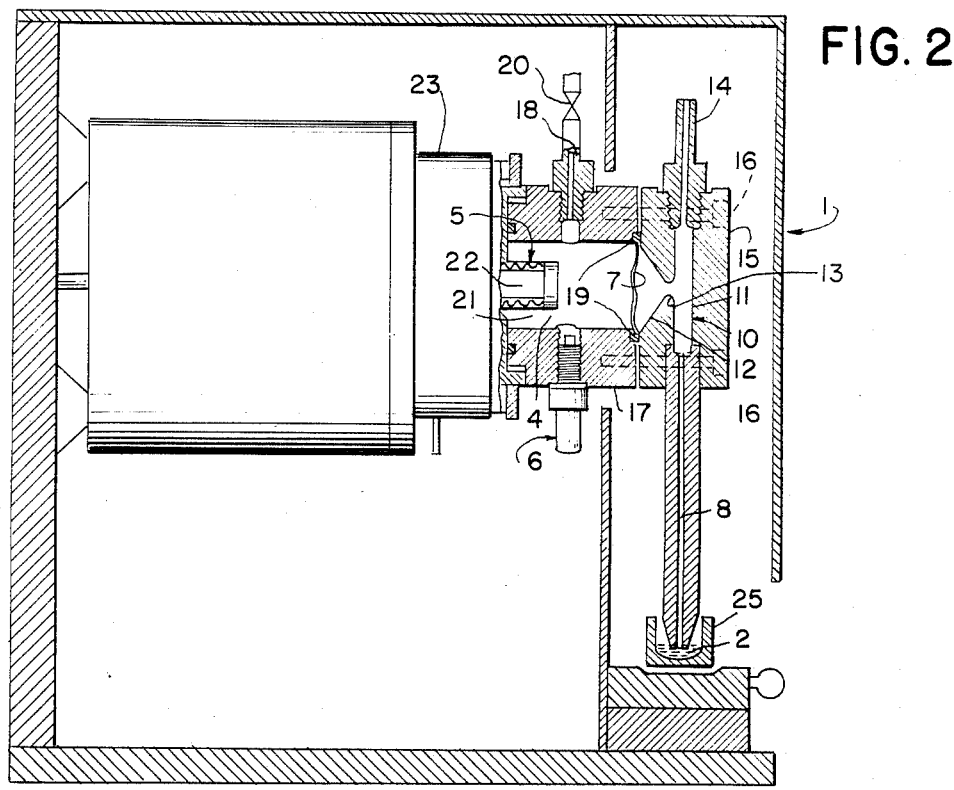

The drawing shows in:

FIG. 1 an apparatus embodying the invention and the schematic connection of a plurality of control-units;

FIG. 2 an enlarged sectional view taken on the line II—II;

FIG. 3 a schematic, enlarged view like FIG. 2;

FIG. 4 a detail corresponding with detail IV of FIG. 3;

FIG. 5 a view corresponding to FIG. 4 in cleaning the measuring tube; and

FIG. 6 a variant of detail VI of FIG. 3.

FIG. 1 shows an apparatus 1 embodying the invention for measuring the viscosity and/or visco-elasticity of a fluid 2, which could for instance be a liquid or a so-called gel. The apparatus 1 comprises a plurality of control-units shown schematically and to be described hereinafter. The apparatus 1 embodying the invention comprises a measuring chamber 4 to be filled with a standard fluid 3, for example, silicon oil, water and the like, comprising pressure generating means 5 and pressure sensing means 6 and a measuring tube 8 connected through a flexible diaphragm 7 with the measuring chamber 4. The measuring tube 8 is in fluid communication with the diaphragm 7 through a coupling chamber 10 to be filled with coupling fluid 9. The coupling chamber 10 comprises a first coupling compartment 11 adjoining the measuring tube 8, a second coupling compartment 12 adjacent the diaphragm 7 and a connecting tube 13 between the first coupling compartment 11 and the second coupling compartment 12, said tube opening out laterally in the first coupling compartment 11. Furthermore the first coupling compartment 11 is provided with a duct 14 opening out therein.

The coupling chamber 10 is formed in a block of material 15 which is arranged with the aid of fastening means 16 on a further block of material 17, whilst between the two blocks of material 15 and 17 the diaphragm 7 is arranged by means of sealing rings 19 in an air- and fluid-tight manner between the measuring chamber 4 and the coupling chamber 10. Since the diaphragm 7 mainly extends in a vertical plane, it is possible to remove air bubbles from the measuring chamber 4 during filling of said chamber through a duct 18 including a valve 20. The pressure generating means 5 are formed by a displacer 21 which is connected through a displacer rod 22 with a unit 23 by which a harmonic or non-harmonic movement is exerted on the displacer 21 in the direction of the double arrow 24. Under the action of this movement the pressure in the measuring chamber 4 varies, which as a result of the fluid contact through the flexible diaphragm 7 with the coupling chamber 4 filled with coupling fluid 9, is mainly determined by the visco-elastic behaviour of the fluid contained in the measuring tube 8.

When calibrating the device embodying the invention the coupling chamber 10 and the measuring tube 8 are filled with coupling fluid, whereas at the subsequent measurements at least the measuring tube 8 is filled with the fluid 2 whose visco-elasticity has to be assessed.

FIG. 3 shows schematically the operation of the apparatus 1 embodying the invention. After the calibration of the apparatus 1 embodying the invention the coupling chamber 10 and the measuring tube 8 are filled with coupling fluid 9. Subsequently, from a holder 25 the fluid 2 to be measured, preceded by separating material 26, in this case an air bubble 27, is passed through the measuring tube 8 into the coupling chamber 10. By the separating material 26 mixing between the coupling fluid 9 and the fluid 2 to be measured is avoided during the transport through the measuring tube 8, which would adversely affect the measurement. Since an inner dimension a of the first coupling compartment 11 is larger than the inner dimension b of the measuring tube 8, the air bubble 27 entering the first coupling compartment 11 will rise in the direction of the arrows 28 across the coupling fluid 9 and will thus be removed from the interface between the fluid 2 and the coupling fluid 9. For this purpose it is, therefore, necessary for the measuring tube 8 to be mainly at a lower level than the measuring chamber 4 and, more particularly at a lower level than the coupling chamber 10. Through the duct 14 and the valve 29 the air bubble 27 leaves the coupling chamber 10 and after the valve 29 is closed, the air bubble 27 can no longer affect the visco-elasticity measurement of the fluid 2.

From the method embodying the invention described above it will be obvious that the measuring tube 8 can be simply and readily filled with the fluid 2 to be measured, whilst an air bubble 27 is used, which in this kind of visco-elasticity measurements may have a detrimental influence on the measuring results. It will furthermore be obvious that with the intermediary of the coupling fluid 9 the apparatus 1 embodying the invention permits of assessing the viscous and/or visco-elastic behaviour of fluids, which might have an adverse effect on the flexible diaphragm, which is preferably made from latex. It is, for example, possible to use isotonic salt solutions, e.g. Ringer solutions having a corrosive effect, for example, due to the salt content. It is furthermore possible to use organic solutions not only as a fluid 2 to be measured but also as a coupling fluid 9, whilst in principle the coupling fluid 9 may have a higher density than the fluid 2 to be measured. In this case the feasability of the measurement depends inter alia on the density differences at the interface and the surface tension between the fluids and the wall material as well as on the configuration of, in particular, the lower end 30 of the coupling chamber 10.

Since the first coupling compartment 11 communicates through the connecting tube 13 with the second coupling compartment 12, it is avoided as far as possible that during the rise of the air bubble 27 as a result of the whirls then occurring in the coupling fluid 9 material would get from the first coupling compartment 11 into the second coupling compartment 12, where it might have a negative effect on the diaphragm 7. A second advantage of this construction will be described further hereinafter.

Through the duct 14 and the valve 29 the coupling chamber 10 is connected via a T-piece 31 with an air pump 32 and a fluid pump 33. With the aid of the fluid pump 33, when the valve 29 is opened, the fluid 2 can be received in the measuring tube 8, the fluid being preceded by an air bubble of predetermined size. After the accomplishment of the measurement part of the coupling chamber 10 and, in particular, the first coupling compartment 11 and part of the connecting tube 13 can be emptied by introducing air 34 with the air of the air pump 32 through the duct 14. This situation is illustrated inter alia in FIG. 5. It will be apparent that an inner dimension a is in this case larger than an inner dimension c of the connecting tube 13, that is to say, to an extent such that as a result of the capillary forces in the connecting tube 13 coupling fluid 9 stays behind, whereas in the first coupling compartment 11 there is only air 34.

When with the aid of the fluid pump 33 an accurately determinable amount of air in the form of the air bubble 27 preceding the fluid 2 to be measured can be received in the measuring tube 8, the air bubble 27 may be present in the coupling chamber 10, when the viscosity and/or visco-elasticity of the fluid 2 is being measured, if it nestles up to a predetermined place, for example, in the vicinity of the valve 29. It is in this case possible to correct effects of the air bubble 27 on the viscosity and/or visco-elasticity measurements, in particular, the pressure differences produced by the pressure generating means 5 (FIG. 4) with the aid of calibration experiments, in which the measuring tube 8 is also filled with coupling fluid 9.

If, contrary to expectation, the second coupling compartment 12 has to be cleaned, for example, because impurities have accumulated therein, the apparatus 1 embodying the invention permits in a very simply manner of cleaning this second coupling compartment 12 because a wall 36 located opposite a side 35 of the diaphragm 7 remote from the measuring chamber 4 is converging in a direction away from the diaphragm 7 and has, for example, a conical shape as shown in FIG. 4. By increasing the pressure in the measuring chamber 4 with the aid of the pressure generating means 5 the diaphragm 7 will smoothly contact the wall 36 and thus remove coupling fluid 9 from the second coupling compartment 12. This coupling fluid 9 can subsequently be removed from the coupling chamber 10 by the cleaning mode described above by using either the air pump 34 or the fluid pump 33.

It will be obvious that also in the known apparatus described above for measuring the viscosity and/or the visco-elasticity of a fluid 2 it is particularly advantageous to use the converging wall 36 for cleaning the volume directly bounding in this case the diaphragm.

As shown in FIG. 6, the use of an air bubble 27 may be dispensed with, if the separating material is formed by piston means 37 which are adapted to reciprocate in the coupling chamber 10, that is to say, the first coupling compartment 11 and the measuring tube 8. The piston means 37 are slidable in sealing relationship in the measuring tube 8 and are drawn up in the first coupling compartment 11 until a sufficient fluid connection is established between the fluid 2 to be measured and the coupling fluid 9, which constitutes in addition the fluid connection with the diaphragm 7 and the standard fluid 3 in the measuring chamber 4.

The apparatus 1 embodying the invention is furthermore provided with a unit 38 for controlling the temperature regime in the apparatus 1, a unit 39 controlling the fluid and air transport through the coupling chamber 10 and the measuring tube 8 with the aid of the air pump 32 and the fluid pump 33, a unit 40 for energizing the pressure generating means 5, for example, for generating a harmonic or non-harmonic oscillation in the standard fluid 3 and finally a flow and pressure measuring unit 41, which is connected with the pressure sensing means 6. By the coupling of the units 39, 40 and 41 in a control-system 42 the viscosity and/or visco-elasticity can be assessed on the basis of the applied movement and the pressure variation resulting therefrom by comparison with calibration data correcting, for example, as the case may be, an air bubble 27 extinguished in the system. Finally the viscosity and/or visco-elasticity measurement can be visualized in the unit 43.

It will be obvious that the impedances of the various parts of the apparatus 1 are chosen so that they do not contribute or at least not in a manner to be corrected to the signal to be measured from which finally the viscosity and/or visco-elasticity of the fluid 2 is assessed.

I claim:

1. Apparatus for measuring the viscosity and/or the visco-elasticity of a fluid comprising: a measuring chamber that can be filled with a standard fluid and is provided with pressure generating means and with pressure sensing means and at least one measuring tube connected through a flexible diaphragm with the measuring chamber for receiving the fluid to be measured, and a coupling chamber that can be filled with a coupling fluid, the coupling chamber being interposed between the measuring tube and the diaphragm.

2. Apparatus as claimed in claim 1, characterized in that the measuring tube is mainly located at a lower level than the measuring chamber.

3. Apparatus as claimed in claim 1, characterized in that the coupling chamber has a first coupling compartment which is connected with the measuring tube.

4. Apparatus as claimed in claim 3, characterized in that the coupling chamber has a second coupling compartment which is adjacent the diaphragm and which is laterally connected with the first coupling compartment.

5. Apparatus as claimed in claim 4, characterized in that a connecting tube connects the first and the second coupling compartment with one another.

6. Apparatus as claimed in claim 3, characterized in that an inner dimension of the first coupling compartment exceeds an inner dimension of the measuring tube.

7. Apparatus as claimed in claim 5, characterized in that an inner dimension of the first coupling compartment is larger than an inner dimension of the connecting tube.

8. Apparatus as claimed in claim 1, characterized in that the diaphragm is mainly located in a vertical plane.

9. Apparatus as claimed in claim 1, characterized in that the coupling chamber is connected to a fluid pump by means of a duct, the duct being provided with a valve.

10. Apparatus as claimed in claim 1, characterized by piston means adapted to reciprocate through the coupling chamber and the measuring tube.

11. Apparatus as claimed in claim 1, characterized in that a wall located opposite a side of the diaphragm remote from the measuring chamber is converging in a direction away from the diaphragm.

12. A method of handling a fluid for measuring the viscosity or visco-elasticity of the fluid comprising the steps of:
   providing an apparatus including a measuring chamber having a standard fluid, a coupling chamber having a coupling fluid, said measuring chamber and coupling chamber being operably connected, and an elongated measuring tube having one end operably connected to the coupling chamber;
   placing the other end of the measuring tube in operable communication with the subject fluid to be measured;
   drawing subject fluid into the measuring tube to fill the measuring tube; and
   filling at least a portion of the coupling chamber with subject fluid to establish an interface between the coupling fluid and subject fluid.

13. A method according to claim 12, including the steps of:

introducing a known pressure to the measuring chamber, the pressure being transmitted to the interface; and sensing the fluid pressure in the measuring chamber.

14. A method according to claim 13, including the step of:

introducing a known fluid flow through the measuring chamber, the flow being transmitted through the interface to the subject fluid;

determining the fluid flow of the standard fluid through the measuring chamber to determine the viscosity or visco-elasticity of the subject fluid.

15. A method according to claim 12, including the steps of:

filling the measuring tube with a fluid of known properties;

calibrating the apparatus in accordance with the fluid of known properties;

expelling the fluid of known properties from the measuring tube.

16. A method according to claim 12, including the steps of:

providing a fluid pump operably coupled to the coupling chamber; and operating the pump to draw the subject fluid into the measuring tube.

17. A method according to claim 12, including the step of:

drawing a gas bubble into the measuring tube prior to drawing subject fluid into the tube.

18. A method according to claim 17, wherein the measuring tube is oriented in a downward direction from the coupling chamber, including the steps of:

allowing the gas bubble to migrate towards an uppermost region of the coupling chamber after the measuring tube is filled with subject fluid; and removing the gas bubble from the coupling chamber.

19. A method according to claim 12, including the steps of:

providing a flexible diaphragm to operably couple and separate the measuring and coupling chambers;

providing the coupling chamber with a converging wall proximate to the diaphragm;

operating the diaphragm to contact the converging wall to dispel any gas bubbles.

20. A method according to claim 12, including the steps of:

providing an elongated plunger sealable in the measuring tube;

operating the plunger in the tube in a direction away from the subject fluid to draw the subject fluid into the tube.

21. A method according to claim 12, including the step of:

placing a separating material in the measuring tube prior to drawing the subject fluid into the tube.

22. A method according to claim 12, including the steps of:

providing a flexible diaphragm to operably couple and separate the coupling and measuring chambers;

operating the diaphragm to manipulate the coupling fluid.

23. A method of handling a fluid for measuring the viscous or visco-elastic properties of the fluid wherein the fluid to be measured is drawn from a holder into a measuring tube and into at least a portion of a coupling chamber attached to the measuring tube, to establish an interface between a coupling fluid and the fluid to be measured in the coupling chamber.

24. A method according to claim 23, wherein a separating material is drawn into the measuring tube preceding the fluid to be measured.

25. The method according to claim 24, wherein the separating material comprises an air bubble.

26. The method according to claim 23, wherein a known pressure and/or known flow is introduced to the interface to produce a pressure and/or flow of the fluid in the measuring tube.

* * * * *